United States Patent
Nehls et al.

(10) Patent No.: US 7,092,759 B2
(45) Date of Patent: Aug. 15, 2006

(54) METHOD OF OPTIMIZING CARDIAC RESYNCHRONIZATION THERAPY USING SENSOR SIGNALS OF SEPTAL WALL MOTION

(75) Inventors: Robert J. Nehls, Lakeville, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 440 days.

(21) Appl. No.: 10/631,551

(22) Filed: Jul. 30, 2003

(65) Prior Publication Data
US 2005/0027320 A1    Feb. 3, 2005

(51) Int. Cl.
*A61N 1/365*    (2006.01)
*A61N 1/368*    (2006.01)
(52) U.S. Cl. .......................................... 607/19; 607/17
(58) Field of Classification Search ............ 607/17–19, 607/9–10, 15; 600/508, 587
See application file for complete search history.

(56) References Cited

U.S. PATENT DOCUMENTS

| | | | |
|---|---|---|---|
| 5,261,418 A | 11/1993 | Ferek-Petric et al. | |
| 5,304,208 A | 4/1994 | Inguaggiato et al. | |
| 5,423,883 A | 6/1995 | Helland | |
| 5,454,838 A | 10/1995 | Vallana et al. | |
| 5,549,652 A | 8/1996 | McClure et al. | |
| 5,628,777 A | 5/1997 | Moberg et al. | |
| 5,693,075 A | 12/1997 | Plicchi et al. | |
| 5,987,352 A | 11/1999 | Klein et al. | |
| 6,044,299 A | 3/2000 | Nilsson | |
| 6,070,101 A | 5/2000 | Struble et al. | |
| 6,077,236 A | 6/2000 | Cunningham | |
| 6,473,645 B1 | 10/2002 | Levine | |
| 2003/0105495 A1* | 6/2003 | Yu et al. .................... | 607/17 |
| 2003/0105496 A1* | 6/2003 | Yu et al. .................... | 607/17 |
| 2004/0019365 A1* | 1/2004 | Ding et al. .................. | 607/17 |
| 2004/0172078 A1* | 9/2004 | Chinchoy ................... | 607/17 |

OTHER PUBLICATIONS

Bongiomi, M.G., et al., "Is Local Myocardial Contractility Related to Endocardial Acceleration Signals Detected by a Transvenous Pacing Lead?" *PACE*, vol. 19, Nov. 1996, Part II, 1682-1688.

(Continued)

*Primary Examiner*—Robert E. Pezzuto
*Assistant Examiner*—Jessica L. Reidel
(74) *Attorney, Agent, or Firm*—Girma Wolde-Michael; Paul H. McDowall (57) ABSTRACT

The present invention relates to monitoring septal wall motion of the atrial and/or ventricular chambers of a heart for optimizing cardiac pacing intervals based on signals derived from the monitored wall motion. At least one lead of medical device is equipped with a motion sensor adapted to couple to septal tissue. The device receives and may post-process (e.g., suitably filter, rectify and/or integrate) motion signals to determine acceleration, velocity and/or displacement. During pacing interval optimization the wall motion is measured for those pacing intervals and the pacing interval setting(s) that produce minimal wall motion for chronic therapy delivery. In addition, methods for periodically determining whether to cease or resume delivery of a bi-ventricular pacing therapy to a patient that may have experienced beneficial reverse remodeling of the heart.

40 Claims, 7 Drawing Sheets

OTHER PUBLICATIONS

Vogel, et al., "Validation of Myocardial Acceleration During Isovolumic Contraction as a Novel Noninvasive Index of Right Ventricular Contractility", *Circulation*, Apr. 9, 2002, pp. 1693-1699.

Bordachar, et al., "Hemodynamic Assessment of Right, Left, and Biventricular Pacing by Peak Endocardial Acceleration and Echocardiography in Patients with End-Stage Heart Failure", *PACE*, vol. 23, Nov. 2000, Part II, pp. 1726-1730.

Padeletti, et al., "Atrioventricular Interval Optimization in the Right Atrial Appendage and Interatrial Septum Pacing: A Comparison Between Echo and Peak Endocardial Acceleration Measurements", *PACE*, vol. 23, Nov. 2000, Part I, pp. 1618-1622.

Plicchi, et al., PEA I and PEA II based implantable haemodynamic monitor: Pre climincal studies in sheet, *Europace*, 2002, vol. 4, pp. 49-54.

Rickards, et al., "An Implantable Intracardiac Accelerometer for Monitoring Myocardial Contractility", *PACE*, vol. 19, Dec. 1996, Part I, pp. 2066-2071.

Leung, et al., "Automatic Optimization of Resting and Exercise Atrioventricular Interval Using a Peak Endocardial Acceleration Sensor . . . ", *PACE*, vol. 23, Nov. 2000, Part II, pp. 1762-1766.

* cited by examiner

METHOD OF OPTIMIZING CARDIAC RESYNCHRONIZATION THERAPY USING SENSOR SIGNALS OF SEPTAL WALL MOTION

CROSS REFERENCE TO RELATED APPLICATIONS

The present patent disclosure relates to and hereby incorporates by reference two non-provisional U.S. patent applications previously invented by E. Chinchoy; namely, application Ser. No. 10/376,981 filed 28 Feb. 2003 entitled, "Method and Apparatus for Assessing Left Ventricular Function and Optimizing Cardiac Pacing Intervals Based on Left Ventricular Wall Motion" and application Ser. No. 10/377,207 filed 28 Feb. 2003 now U.S. Pat. No. 6,885,889, entitled, "Method and Apparatus for Optimizing Cardiac Resynchronization Therapy Based on Left Ventricular Acceleration."

FIELD OF THE INVENTION

The present invention relates to the field of cardiac therapy. In particular, the present invention provides methods and apparatus for measuring displacement of cardiac tissue which measurement may be used to optimize certain forms of bi-ventricular cardiac therapy, such as cardiac resynchronization therapy (CRT).

BACKGROUND OF THE INVENTION

Those skilled in the art of diagnosing cardiac ailments have long understood that certain patients, in particular heart failure (HF) patients, suffer uncoordinated mechanical activity wherein the myocardial depolarization and contraction of the right and left ventricle do not occur simultaneously. Such uncoordinated motion causes a decrease in cardiac output (CO), among other detrimental effects. Recently a variety of techniques have been proposed and practiced for minimizing such uncoordinated motion and increasing CO.

These prior art techniques for minimizing ventricular uncoordinated motion include CRT. In some forms of CRT, pressure-based measurements in one or both ventricles have been known and used for some time. In such methods, a pressure transducer is typically coupled to the distal end of a medical electrical lead used to measure intraventricular pressure variations. Such measured variations (maximum, minimum, calculated first derivatives thereof, etc.) provide feedback to an implantable pulse generator (IPG) programmed to deliver CRT. Such an IPG typically includes at least three medical electrical leads coupled to cardiac tissue. A first lead typically coupled to the right atrium, a second lead typically coupled to the right ventricle, and a third lead typically coupled to the left ventricle (often via the coronary sinus or great vein). That is, the third lead often couples to a location on the free wall of the left ventricle.

Thus, as is known in the art, based at least in part on the pressure-based measurements the IPG provides electrical cardiac pacing stimulus to the left ventricle (LV) and the right ventricle (RV) in an effort to suitably increase the measured pressure(s) and/or derivatives thereof.

When successfully delivered, CRT is known to increase CO and may, over time, cause a phenomenon known in the art as "reverse remodeling" of the LV and RV (and/or other beneficial) physiologic changes to the patient's heart.

The inventors are also aware of another technique for CRT for HF patients; namely, using an accelerometer disposed in the apex of the right ventricle to measure endocardial acceleration of the apical portion of the right ventricle. From this measurement in the right ventricle a left ventricular activity is inferred. However, to the best knowledge of the inventors such technique has not been used to directly measure deflection of the ventricular or atrial septal wall in patients afflicted with uncoordinated ventricular motion and the like.

SUMMARY OF THE INVENTION

The present invention addresses the above described needs by providing means for detecting uncoordinated ventricular motion, monitoring or measuring septal wall deflection due to ventricular uncoordinated motion, and/or reducing said uncoordinated motion with appropriately timed electrical stimulation coupled to both ventricular chambers to decrease said uncoordinated motion and increase cardiac output.

That is, the present invention provides novel methods and apparatus for measuring septal wall deflection in a closed-loop system including an IPG to thereby provide automatic optimization of inter-atrial (A—A) pacing intervals and/or interventricular (V—V) pacing intervals to minimize uncoordinated cardiac motion and improve CO, among other advantages. The present invention thus provides means for reducing: intra-atrial uncoordinated motion and intra-ventricular uncoordinated motion (A—A and V—V uncoordinated motion, respectively), as well as atrio-ventricular uncoordinated motion (i.e., A-V and V-A uncoordinated motion).

In embodiments of the present invention directed to reducing A—A uncoordinated motion an additional lead should be electrically coupled to the left atrium (LA). In one implementation of the present invention, if desired, a variety of respective intraventricular timing can be implemented so that an LV depolarization is timed to slightly precede an RV depolarization (or vice versa). That is, if due to physiologic cardiac characteristics—or other confounding factors—for a particular patient the timing of a discrete cardiac pacing pulse to the LV may need to be slightly offset from a corresponding cardiac pacing pulse delivered to the RV to minimize deflection of the ventricular septal wall. This optimization modality is believed to be highly effective in promoting beneficial, synchronized cardiac depolarization events, especially for HF patients.

In one form of the invention, septal wall deflection is measured by an accelerometer coupled to a portion of septal wall tissue. The accelerometer may comprise a single- or multiple-axis accelerometer. In the event that a single-axis accelerometer is used its axis ought to be transverse to the longitudinal axis of an elongated cardiac sense/pace (or dedicated) medical electrical lead. As a result, when the lead is disposed along the RV outflow tract (RVOT) the single-axis of the accelerometer will be substantially perpendicular to the plane of adjacent septal wall tissue and will provide a more reliable measurement of septal tissue motion. However, a multi-axis accelerometer may be coupled to an intermediate portion of an elongated medical lead adapted to actively affix the accelerometer to the septal wall at any convenient, oblique angle relative to the adjacent septal wall tissue. In any event, the choice of transducer has a bearing on the location and configuration of the accelerometer with respect to the tissue of the septal wall to which the lead is affixed. Any distal portion of the lead with respect to the accelerometer should have sufficient resiliency in the longitudinal axis to accurately convey deflection forces from the septal wall to the accelerometer.

A temporal window during which a useful signal may be obtained should be defined. If the window is accurately defined the duty cycle of the transducer and attendant computational overhead (and related energy drain) can be minimized. Alternatively, constant measuring, signal filtering, mathematical integrating (if applicable) and comparing the resulting signals to choose optimum pacing intervals may be employed. However, one reliable technique for defining the temporal window is to simply trigger the motion measurements from detected cardiac cycle activity. An atrial or ventricular electrogram, or other sensing vector(s) may be used. For example, a trigger event may comprise a sensed, intrinsic or evoked atrial or ventricular event with a programmable or predetermined motion-sensing-delay interval added so that the temporal motion-sensing window can begin and end when the septal wall motion is most likely to be of interest. Another technique to define the temporal window is to trigger from a maximum motion signal and, optionally, add a motion-sensing-delay before beginning to track signals related to motion of septal wall tissue. Since the present invention is directed at minimizing septal wall motion, a fiducial or reference point may effectively comprise a maximum magnitude acceleration signal.

In one form of the present invention the accelerometer may be combined into a single sensing cell having at least one additional physiologic sensor, such as a pressure sensor, disposed or coupled thereto. In this form of the invention, the pressure sensor can be spaced from the septal wall proximal the accelerometer, although such a configuration is not required. In an alternative form of the invention temperature sensor(s) may be electrically and/or mechanically coupled to the accelerometer and/or the canister for the IPG or to one of the other medical leads coupled to the IPG. Such sensors may provide direct venous or arterial temperature measurements and/or indirect measurement of cardiac function such as fluid flow, velocity, and the like.

In another form of the present invention, a primary accelerometer may be coupled to a portion of the atrial or ventricular septal wall and additional accelerometer(s) may be coupled to another portion of cardiac tissue. For example, an additional accelerometer may be coupled to a portion of RV endocardial tissue opposing the primary accelerometer. The output signals from such additional accelerometer units may be provided directly or in combination with other of the output signals from accelerometer or other physiologic sensors. That is, relatively excessive motion (i.e., acceleration, velocity or displacement) of the septal wall in combination with limited "motion" or measurable output signal related to the function of RV or LV tissue spaced from the septal wall may indicate uncoordinated V—V motion causing inefficient function during respective depolarization of the LV and RV. In the event that a pressure signal is measured adjacent an accelerometer, an additional component of the mechanical uncoordinated motion may be revealed.

According to the present invention, multiple-axis accelerometers may be used in conjunction with or in lieu of single-axis accelerometers. If a three-axis accelerometer is coupled to tissue opposing the septal wall tissue then an essentially three-dimensional (3D) representation or motion model may be determined. For example, if a single-axis accelerometer coupled to septal wall tissue indicates relatively limited displacement while a three-axis accelerometer coupled to the LV free wall indicates a non-linear "loop motion" displacement of the septal wall tissue, such mechanical uncoordinated motion may be more accurately determined. With additional empirical study, such motion may provide a strong correlation to one or more New York Heart Association (NYHA) HF classifications (e.g., Class I, II, II, IV and/or so-called "end-stage heart failure").

With respect to the closed-loop CRT optimization methods and apparatus, in addition to detecting (diagnosing) cardiac mechanical dysfunction and/or providing a correlation between sensed linear or non-linear acceleration (i.e., motion due to displacement) of the septal wall of a patient and NYHA Class of said patient, the present invention also provides automatically optimized, dynamically-adjustable CRT pacing modalities. In essence, one basic embodiment of the present invention provides A—A, A-V interval timing and/or V—V interval timing to minimize atrial and/or ventricular septal wall displacement.

This interval timing can be viewed as "delay intervals" with respect to an initial intrinsic or evoked depolarization of one or more chambers of a patient's heart. The displacement sensed by one or more accelerometers may be directly provided to suitable CRT (or other pacing modality) timing circuitry and/or a first, second or other derivative (or integral) results calculated therefrom.

DETAILED DESCRIPTION OF THE INVENTION

As indicated above, the present invention is directed toward providing a method and apparatus for optimizing ventricular function and selecting cardiac pacing intervals for the purposes of restoring normal ventricular synchrony based on monitoring septal wall motion. The present invention is useful in optimizing atrial-ventricular, inter-atrial and inter-ventricular pacing intervals during cardiac resynchronization therapy (CRT) used for treating heart failure. The present invention is also useful in selecting pacing parameters used during temporary pacing applied for treating post-operative uncoordinated cardiac chamber (e.g., atrial and/or ventricular) motion. As such, the present invention may be embodied in an implantable cardiac pacing system including a dual chamber or multichamber pacemaker and associated set of medical electrical leads. Alternatively, the present invention may be embodied in a temporary pacing system including an external pacing device with associated temporary pacing leads.

Figure 1:
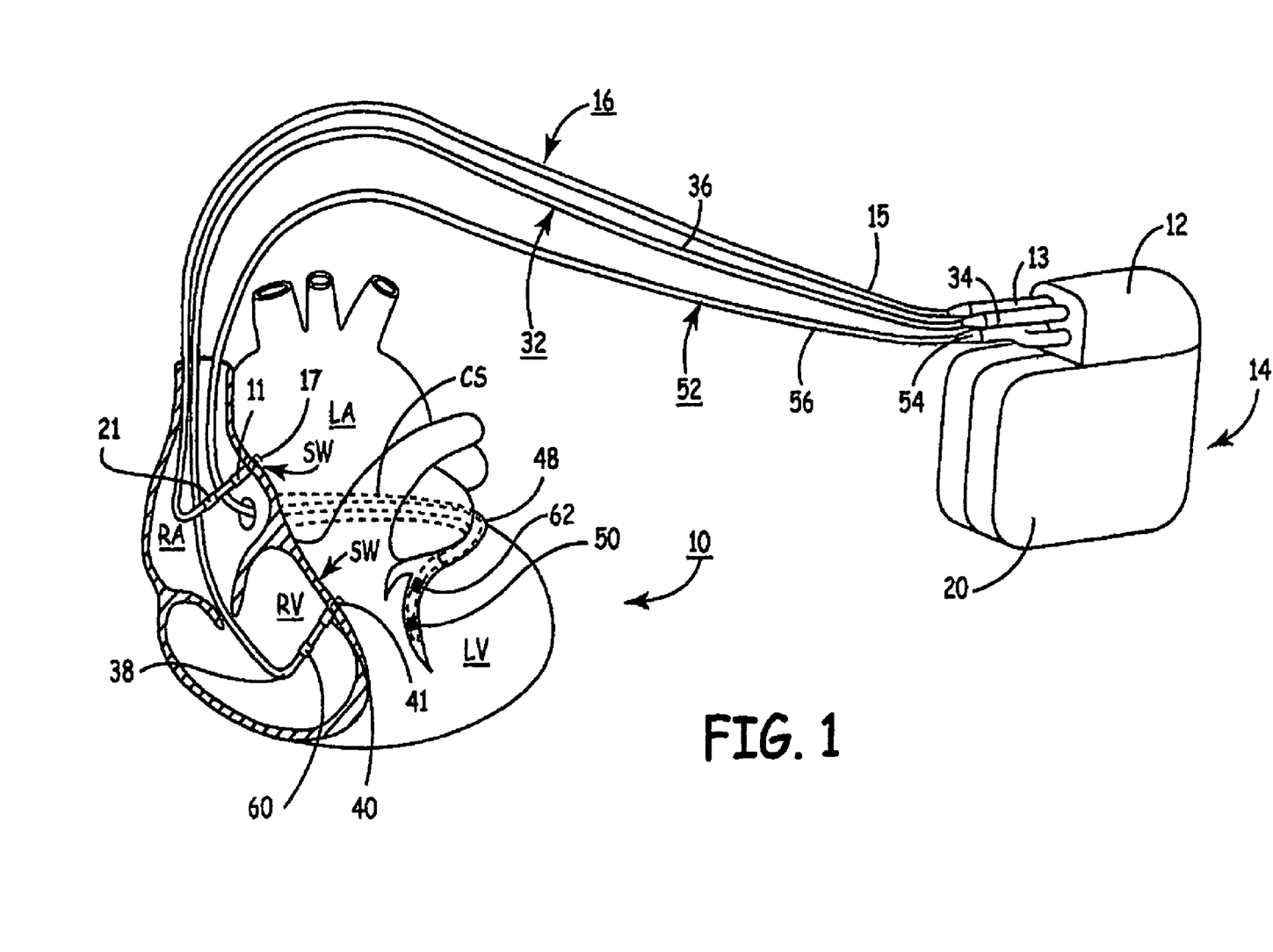
FIG. 1 depicts an exemplary implantable, multi-chamber cardiac pacemaker coupled to a patient's heart via transvenous endocardial leads.

FIG. 1 depicts an exemplary implantable, multi-chamber cardiac pacemaker 14 in which the present invention may be implemented. The multi-chamber pacemaker 14 is provided for restoring ventricular synchrony by delivering pacing pulses to one or more heart chambers as needed to control the heart activation sequence. The pacemaker 14 is shown in communication with a patient's heart 10 by way of three leads 16, 32 and 52. The heart 10 is shown in a partially cut-away view illustrating the upper heart chambers, the right atrium (RA) and left atrium (LA) and septal wall (SW) disposed therebetween, and the lower heart chambers, the right ventricle (RV) and left ventricle (LV) and the septal wall (SW) disposed therebetween, and the coronary sinus (CS) extending from the opening in the right atrium laterally around the atria to form the great cardiac vein 48, which branches to form inferior cardiac veins.

The pacemaker 14, also referred to herein from time to time as an implantable pulse generator (IPG) or an implantable cardioverter-defibrillator (ICD), is implanted subcutaneously in a patient's body between the skin and the ribs. Three transvenous-endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 is attached to the RA wall by an attachment mechanism 17. The attachment mechanism may be active or passive as is known in the art and as may be later developed. A helix or tined lead may be used as is known in the art, to adapt the distal end of an accelerometer-bearing lead for relatively permanent fixation to septal wall tissue. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 17 and proximal ring RA pace/sense electrode 21 provided for achieving RA pacing and sensing of RA electrogram (EGM) signals. In certain embodiments of the present invention, a motion sensor 11 such as a single- or multi-axis accelerometer is coupled to the lead 16 proximal the attachment mechanism 17. In such embodiments, the attachment mechanism 17 is adapted to couple to a portion of septal tissue of the RA wall so that the motion sensor 11 provides a signal related to atrial septal wall motion. Off-axis (or radial) accelerometer data may not be as valuable in assessing wall motion and optimizing pacing intervals as on-axis (or longitudinal) data; therefore, a single or uniaxial accelerometer performs adequately according to the present invention.

In accordance with a triple chamber embodiment of the present invention, a coronary sinus lead 52 capable of stimulating the left ventricle is preferably of a relatively small size and diameter such that it may be passed through the coronary sinus and entering a vessel branching from the great cardiac vein and able to be steered to a left ventricular pacing site.

Sensor 60 may alternatively be provided as another type of sensor such as an optical, acoustical, or Hall effect sensor or a sensor having piezoelectric, inductive, capacitive, resistive, or other elements which produce a variable signal proportional to septal wall motion or acceleration. Sensor 60 is preferably located on lead 32 such that when the lead is positioned for pacing and sensing, sensor 60 is located approximately near the RV outflow tract (RVOT) so that relatively high fluid flow helps decrease deleterious fibrotic growth.

The depicted positions of the leads and electrodes shown in FIG. 1 in or about the right and left heart chambers are approximate and merely exemplary. For example, a motion sensor 11,60 may alternatively be located on a dedicated lead (not shown) such that the motion sensor 11,60 is the only component of the dedicated lead. In addition, the motion sensor 11,60 may be coupled to one or more defibrillation electrodes (e.g., high voltage coils) or an additional sensor capsule (e.g., a pressure sensor, a pH sensor, and the like) positioned in a spaced-apart relation to the motion sensor 11,60, or in any accessible endocardial location. Furthermore, it is recognized that alternative leads and pace/sense electrodes that are adapted for placement at pacing or sensing sites on or in or relative to the RA, LA, RV and LV may be used in conjunction with the present invention.

This atrial septal wall motion signal from motion sensor 11, alone or in combination with a ventricular septal wall motion signal from motion sensor 60 (described below), is provided to pacing stimulus timing circuitry of the IPG 14 so that pacing stimulus is provided to minimize at least a portion of the respective wall motion signal(s). For example, according to the present invention septal wall motion signals corresponding to the isovolumic contractile phase of the cardiac cycle, a whole-cycle signal, a P-wave depolarization, an R-wave depolarization, and/or a filtered and/or rectified portion of the foregoing may be used to suitably administer the pacing stimulus.

Bipolar, endocardial RV lead 32 passes through the RA into the RV where its distal ring and tip RV pace/sense electrodes 38,40 are adapted for fixation to a portion of ventricular septal wall tissue by a distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 41 and proximal ring RV pace/sense electrode 38 provided for RV pacing and sensing of RV EGM signals. RV lead 32 may optionally include a RV septal wall motion sensor 60. RV septal wall motion sensor 60 may be positioned into or proximate a portion of the intraventricular septum for detecting motion or acceleration of the intraventricular septal tissue. Implantation of an acceleration sensor in the right ventricle, albeit in an apical portion of the RV, is generally disclosed in the above-cited U.S. Pat. No. 5,693,075 issued to Plicchi, et al.

In the illustrated embodiment of a triple chamber IPG capable of delivering CRT, a unipolar or bipolar or multi-polar endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of IPG connector block 12. A small diameter unipolar lead body 56 is selected in order to lodge the distal LV CS pace/sense electrode 50 deeply in a cardiac vein branching from the great cardiac vein 48.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductor extending proximally from the more proximal LA CS pace/sense electrode(s) and terminating in a bipolar connector 54.

Figure 2:
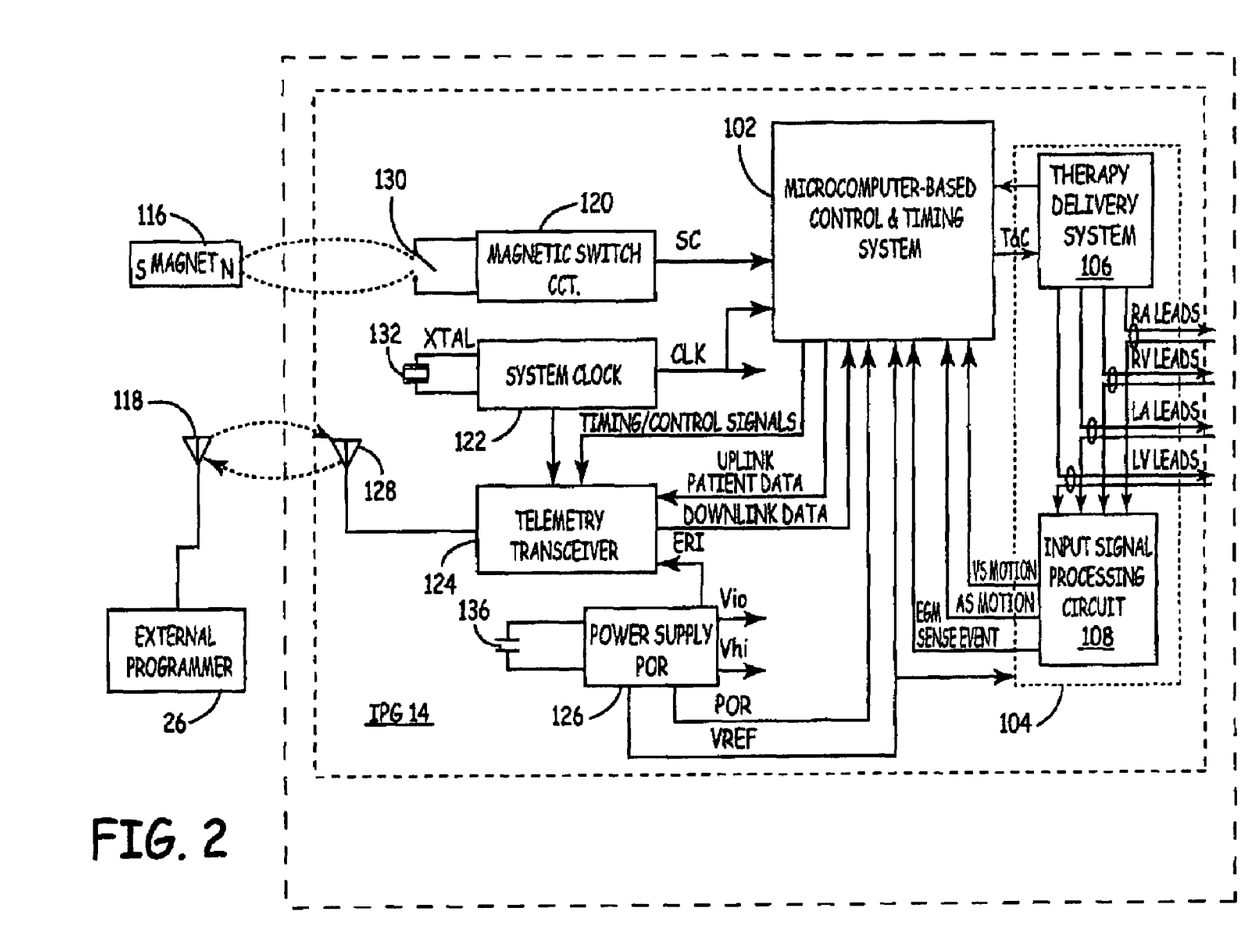
FIG. 2 is a schematic block diagram of the multi-chamber pacemaker of FIG. 1 capable of delivering a resynchronization therapy and processing left ventricular wall motion sensor signal input.

FIG. 2 is a schematic block diagram of an exemplary multi-chamber IPG 14, such as that shown in FIG. 1, that provides delivery of a resynchronization therapy and is capable of processing atrial and/or ventricular septal wall motion sensor signal input. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize depolarization of chambers of a patient's heart. The interface circuitry 104 therefore includes a therapy delivery system 106 intended for delivering cardiac pacing impulses under the control of control and timing system 102. Delivery of pacing pulses to two or more heart chambers is controlled in part by the selection of programmable pacing intervals, which can include atrial-atrial (A—A), atrial-ventricular (A-V), and ventricular-ventricular (V—V) intervals.

Physiologic input signal processing circuit 108 is provided for receiving cardiac electrogram (EGM) signals for determining a patient's heart rhythm. Physiologic input signal processing circuit 108 additionally receives signals from at least one septal wall motion sensor 11,60 and processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, wall motion sensors, and any other physiological sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable pacing intervals is preferably based on a determination of right ventricular septal wall motion derived from sensor 62 signals as will be described in greater detail below.

The therapy delivery system 106 can optionally be configured to include circuitry for delivering cardioversion/defibrillation therapy in addition to cardiac pacing pulses for controlling a patient's heart rhythm. Accordingly, as previously mentioned medical electrical leads in communication with the patient's heart could also advantageously include high-voltage cardioversion or defibrillation shock electrodes.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber pacemaker circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, wall motion signals, and/or relating to device operating history or other sensed physiologic parameters for uplink telemetry transmission upon receipt of a retrieval or interrogation instruction via a downlink telemetry transmission. Criteria for triggering data storage can be programmed via down linked instructions and parameter values. Physiologic data, including septal wall motion data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or septal wall motion data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sensed events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an atrial sense or ventricular sense event signal to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect. The intervals at which pacing pulses are delivered are preferably determined based on an assessment of septal wall motion data.

As such, input signal processing circuit 108 further includes signal processing circuitry for receiving, amplifying, filtering, averaging, digitizing or otherwise processing the wall motion sensor signal. If additional wall motion sensors 11,60 are included in the associated lead system, for example a RV or LV wall motion sensor, additional wall motion signal processing circuitry may be provided as needed. Wall motion signal processing circuitry is further provided for detection and/or determination of one or more wall motion signal characteristics such as maximum and minimum peak amplitudes, slopes, integrals, or other time or frequency domain signal characteristics that may be used as indices of wall motion or correlates to hemodynamic performance. Such wall motion signal characteristic values determined from a ventricular septal wall motion sensor signal are made available to control and timing system 102 via a ventricular-septal motion signal line (designated "VS MOTION") in FIG. 2 for use in algorithms performed for identifying pacing intervals producing optimal ventricular-septal wall motion. If an atrial wall motion sensor is present, an additional atrial-septal motion signal line (designated "AS MOTION") provides atrial-septal wall motion signal data to control and timing system 102.

Figure 3:
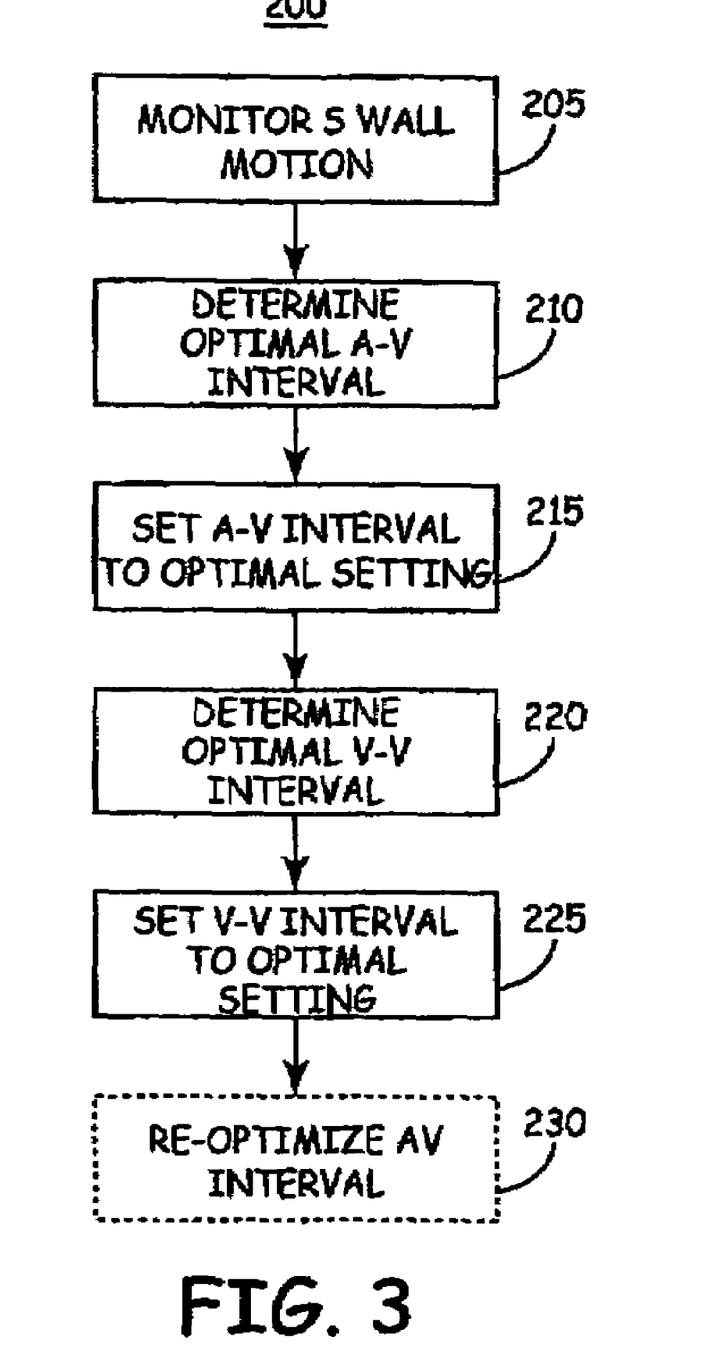
FIG. 3 is a flow chart providing an overview of a method for optimizing cardiac pacing intervals based on monitoring septal wall motion.

FIG. 3 is a flow chart providing an overview of a method for optimizing cardiac pacing intervals based on monitoring septal wall motion. Method 200 begins at step 205 by monitoring septal wall motion. Preferably a wall motion sensor is implanted in or proximate to the septal free wall as described above.

At step 210, an optimal A-V interval is determined if the pacing mode is an atrioventricular or atrio-biventricular or biatrial-biventricular mode. Depending on the dual chamber or multichamber pacing system being used, a right A-V interval or a left A-V interval or both may be determined. For the embodiment shown in FIG.1 A, an optimal right atrial to right ventricle interval is determined. However, in other embodiments, the left atrial-left ventricular interval is optimized based on septal wall motion to ensure optimal filling of the LV. A method for determining an optimal A-V interval based on septal wall motion will be described in conjunction with FIG. 5. At step 215, the A-V interval is automatically adjusted to the optimal A-V interval determined at step 210.

At step 220, the optimal V—V interval is determined for bi-ventricular or atrio-biventricular pacing modes. A method for optimizing the V—V interval based on septal wall motion will be described in conjunction with FIG. 6. At step 225, the V—V interval is automatically adjusted to the optimal V—V interval determined at step 220. After adjusting the V—V interval, an optional step 230 may be performed to re-optimize the A-V interval. Verification of the provisionally determined optimal A-V interval is made by re-determining the optimal A-V interval during biventricular pacing at the newly optimized V—V interval. The A-V interval may be re-adjusted accordingly if a different A-V interval is identified as being optimal during pacing at the optimal V—V interval.

Figure 4:
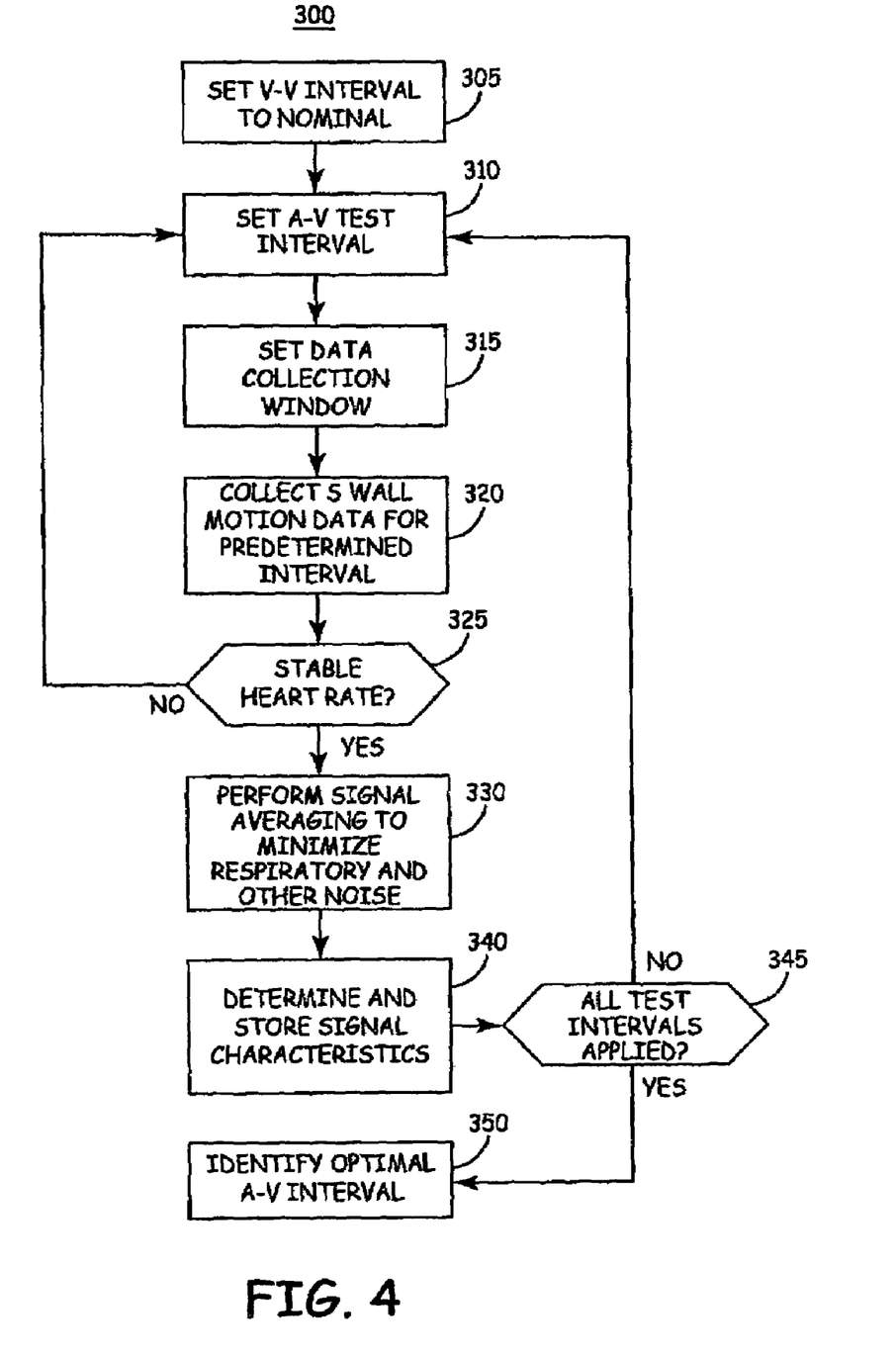
FIG. 4 is a flow chart summarizing steps included in a method for determining an optimal AV interval based on left ventricular wall motion for use in the method of FIG. 3.

FIG. 4 is a flow chart summarizing steps included in a method for determining an optimal AV interval based on septal motion for use in method 200 of FIG. 3. Method 300 begins at step 305 by setting a desired pacing interval (e.g., an A—A, A-V, V-A or V—V interval) to a nominal setting. For example, a nominal V—V interval setting of zero ms may be used so that the left and right ventricles are paced simultaneously while measuring accelerometer signals during subsequent cardiac cycles. To the extent that physiologically related intervals are to be optimized, any intervals related to atrial activation can be optimized before any intervals related to ventricular activity. However, the present invention is not to be viewed as so limited. In FIG. 4 and as shown at step 310, optimization of an A-V interval may be set. Accordingly, a number of predetermined test A-V intervals are iteratively programmed and resulting accelerometer signals measured, collected and compared.

In a patient with intact atrioventricular conduction, the A-V intervals tested may include the intrinsic A-V interval. In order to allow intrinsic A-V conduction, the A-V interval is set at a maximum setting or a setting longer than the intrinsic A-V conduction time. The intrinsic A-V conduction time may be determined by measuring the interval from an atrial pacing pulse to a subsequently sensed R-wave. Remaining test A-V intervals may be applied at decreasing increments from the intrinsic A-V interval. Alternatively, test A-V intervals may be applied randomly ranging from 0 ms to the intrinsic A-V interval. If atrioventricular conduction is not intact, a set of test A-V intervals may be selected over a predefined range, for example a range from 0 ms to on the order of 250 ms.

At step 315 a data collection window is set. Septal wall motion data is preferably collected during systolic contraction such that acceleration or motion of the septal wall over which the wall motion sensor is positioned may be measured. However, septal wall motion data may be acquired for use in assessing cardiac function or optimizing a therapy during the isovolumic contraction phase, the ejection phase, isovolumic relaxation, early diastolic filling, and/or late diastolic filling. The data collection window may be a fixed time interval following a delivered ventricular or atrial pacing pulse (or sensed R-wave if intrinsic A-V conduction is being tested in patients without AV block). A data collection window may be set as a time interval beginning at the delivery of a ventricular pacing pulse with a duration on the order of 30 to 180 ms, for example.

At step 320, the septal wall motion signal is sampled during the data collection window for each cardiac cycle during a predetermined time interval or for a predetermined number of cardiac cycles. In an alternative embodiment, the septal wall motion signal may be acquired continuously during the predetermined time interval or number of cardiac cycles and subsequently processed to separate components associated with the maximum acceleration phase of the systolic contraction. The time interval or number of cardiac cycles preferably extends over at least one respiration cycle such that averaging of the septal wall motion signal over a respiration cycle may be performed to eliminate variations in the septal wall motion measurements due to respiration. In one embodiment, the start and stop of wall motion data acquisition may be triggered by sensing a respiration cycle. Respiration may be detected based on impedance measurements or other methods known in the art.

At decision step 325, verification of a stable heart rate during the data acquisition interval is performed. Heart rate instability, such as the presence of ectopic heart beats or other irregularities, would produce anomalous septal wall motion data. As such, the heart rate preferably stays within a specified range. In one embodiment, heart rate stability may be verified by determining the average and standard deviation of the cardiac cycle length during the data acquisition period. The cardiac cycle length may be determined as the interval between consecutive ventricular events including ventricular pacing pulses and any sensed R-waves. If the average cardiac cycle length or its standard deviation falls outside a predefined range, the data is considered unreliable. Data acquisition may be repeated by returning to step 315 until reliable data is collected for the current test interval setting.

At step 330, signal averaging is performed to minimize the effects of respiration-related or other noise. The signals acquired during each cardiac cycle over the data collection interval are averaged to obtain an overall average septal wall motion signal. At step 340, one or more signal features are determined from the averaged signal as a measurement of septal wall motion and stored in device memory with corresponding test interval information. Preferably, the maximum amplitude of an accelerometer signal or its maximum excursion determined as the difference between the maximum and minimum peak amplitude, also referred to herein as "peak-to-peak difference" is determined as a measure of the maximum acceleration of the septal wall segment during systole. In one embodiment, the maximum peak amplitude or peak-to-peak difference of an accelerometer signal during isovolumic contraction is used as a metric of cardiac function. Other septal wall motion signal features may additionally or alternatively be determined as indices of LV mechanical function or hemodynamic correlates. Other septal wall motion signal features that may be derived include, but are not limited to, a slope, an integral, a frequency component, or other time or frequency domain characteristics.

If all test A-V intervals have not yet been applied, as determined at decision step 345, the method 300 returns to step 310 to adjust the A-V interval to the next test setting. Once all test A-V intervals have been applied, the optimal A-V interval is identified from the stored septal wall motion data at step 350.

Figure 5:
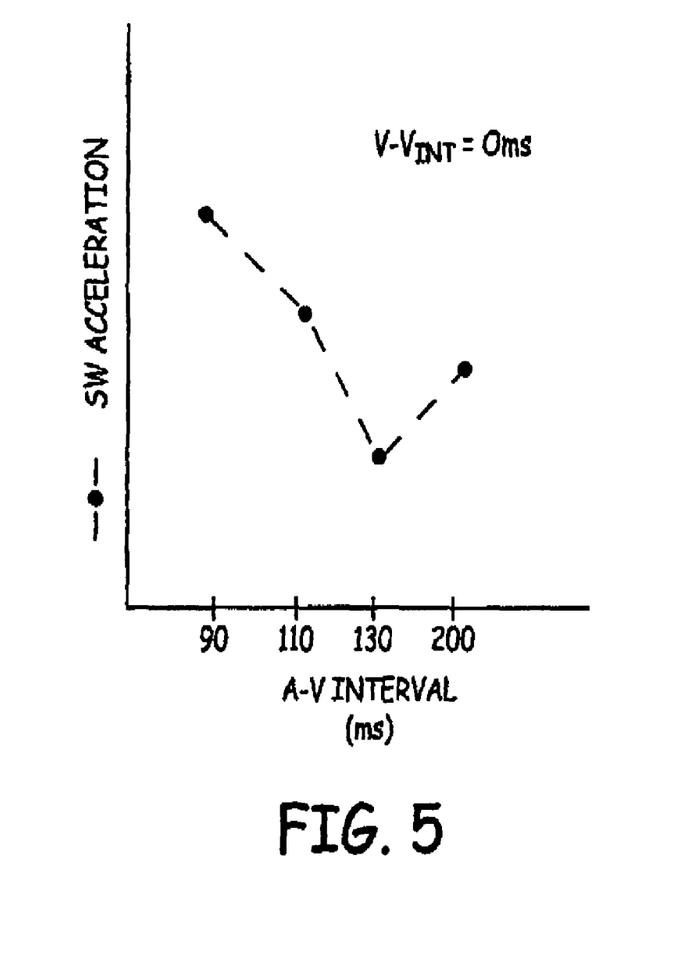
FIG. 5 is a graph of representative septal wall motion that illustrates accelerometer signal output during atrio-biventricular pacing at varying A-V intervals and simultaneous right and left ventricular pacing (V—V interval set to 0 ms).

FIG. 5 is a graph of representative septal wall (SW) motion that illustrates accelerometer signal output during atrio-biventricular pacing at varying A-V intervals and simultaneous right and left ventricular pacing (V—V interval set to 0 ms). As A-V interval is increased from 90 ms to 200 ms, the maximum septal wall acceleration and peak-to-peak acceleration decrease to a local minimum or fiducial point (or "saddle point" at 130 ms) then increase again. In one embodiment, the optimal A-V interval is selected as an A-V interval corresponding to a local minimum (as depicted by a fiducial point) found by plotting a septal wall motion parameter (e.g., acceleration, velocity, or displacement) as a function of A-V interval. In the example shown in FIG. 5, the derived parameter is an acceleration signal produced by an accelerometer coupled to a portion of septal wall tissue. Based on this parameter, and the criteria described above, an optimal A-V interval can be identified as 130 ms. According to the present invention, the optimal A-V interval is the interval corresponding to minimal motion of the septal wall.

When method 300 is executed by an external pacing system, septal wall motion data may be displayed in real-time or stored and presented following an optimization procedure. When method 300 for identifying an optimal A-V interval is executed by an implanted device, septal wall motion data may be stored for later uplinking to an external device for display and review by a physician. After identifying the optimal A-V interval, the A-V interval setting may be automatically adjusted according to method 200 described above.

Figure 6:
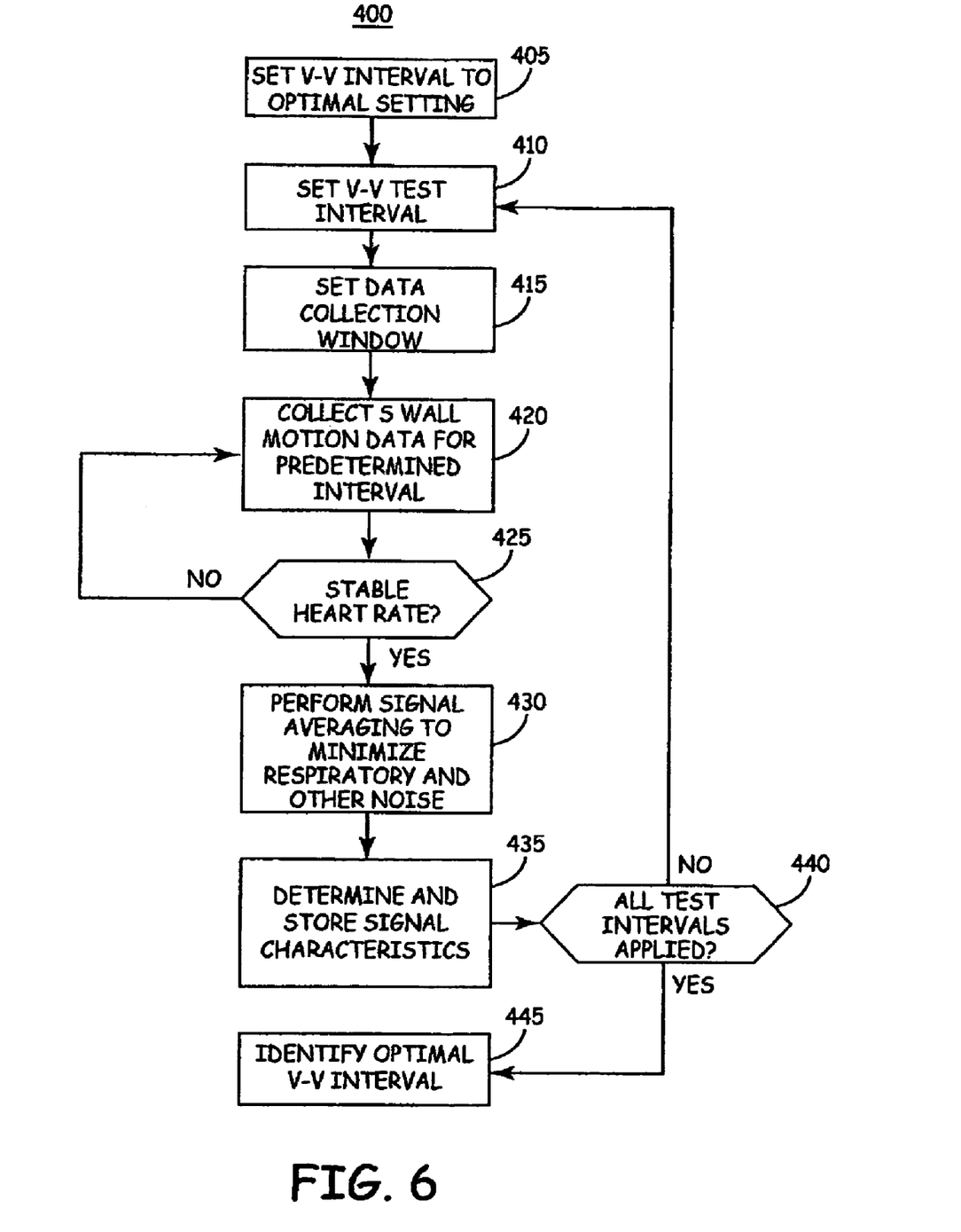
FIG. 6 is a flow chart summarizing steps included in a method for determining an optimal V—V interval based on septal wall motion for use the method FIG. 3.

FIG. 6 is a flow chart summarizing steps included in a method for determining an optimal V—V interval based on left ventricular wall motion for use in method 200 of FIG. 3. At step 405, the A-V interval is programmed to an optimal setting determined according to method 300 of FIG. 3. At step 410, the V—V interval is set to a test interval. A range of test intervals are predefined and may be delivered in a random, generally increasing, or generally decreasing fashion. A range of test intervals may include intervals that result in the right ventricle being paced prior to the left ventricle and intervals that result in the left ventricle being paced prior to the right ventricle. A set of exemplary test intervals includes right ventricular pacing 20 ms and 40 ms prior to left ventricular pacing, simultaneous left and right ventricular pacing (a V—V interval of 0 ms), and left ventricular pacing 20 ms and 40 ms prior to the right ventricle.

Method 400 proceeds to determine the optimal V—V interval in a manner similar to method 300 for determining the optimal A-V interval described above. A data collection window is set at step 415, and septal wall motion data is collected for a predetermined time interval or number of cardiac cycles at step 420 during the data collection window applied to each cardiac cycle. After verifying a stable heart rate at step 425, signal averaging is performed at step 430 allowing an average peak amplitude or average peak-to-peak difference or other signal characteristic to be determined at step 435. After all test V—V intervals are applied as determined at decision step 440, the optimal V—V interval is identified at step 445.

Figure 7:
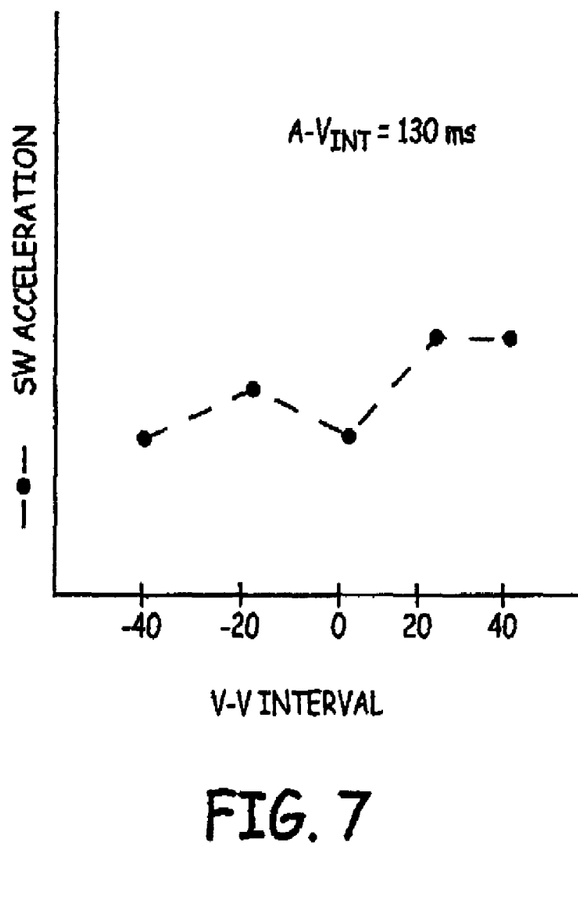
FIG. 7 is a graph of representative septal wall motion that illustrates accelerometer signal output during atrio-biventricular pacing at varying V—V intervals (and an A-V interval, previously optimized to 130 ms).

FIG. 7 is a graph of representative septal wall motion that illustrates accelerometer signal output during atrio-biventricular pacing at varying V—V intervals (and an A-V interval, previously optimized to 130 ms as depicted in FIG. 5). As is known in the art, simultaneous RV and LV pacing occurs at a V—V interval of 0 ms. By arbitrary convention, negative V—V intervals indicate LV pacing prior to RV pacing, and a positive V—V interval indicates RV pacing prior to LV pacing. According to the present invention, the optimal V—V interval is selected as the interval producing the minimum septal wall motion (e.g., acceleration, velocity, or displacement) based on the minimum peak amplitude, peak-to-peak difference, or based on a local minimum (or fiducial point) of an accelerometer signal over a predetermined range of V—V interval values. In the example shown, the optimal V—V interval may be identified, based on minimal septal acceleration, as a negative twenty (−20) ms interval (by convention, the RV with the LV paced 20 ms prior to the RV. Of course, while not depicted in FIG. 7 (or FIG. 5) the present invention may be used to optimize A—A and V-A intervals for a variety of multi-chamber pacing modalities, including a quadruple chamber pacing modality.

When method 400 is executed by an external pacing system, septal wall motion data may be displayed in real-time or stored and presented following an optimization procedure. When method 400 for identifying an optimal V—V interval is executed by an implanted device, septal wall motion data may be stored for later uplinking to an external device for display and review by a physician. After identifying the optimal V—V interval, the V—V interval setting may be automatically adjusted according to method 200 described above.

As noted previously, after adjusting the V—V interval to an optimal setting, verification that the A-V interval is still optimal may be desired (step 230, FIG. 3). In order to re-optimize the A-V interval, method 300 may be performed as described above with the V—V interval programmed to the optimal setting identified by method 400 rather than a nominal setting. If a different A-V interval is found to be optimal, the A-V interval setting may be adjusted appropriately.

It is contemplated that optimization of A-V and V—V intervals based on septal wall motion according to the methods above may be performed in conjunction with an assessment of other wall segment motion, such as the RV apex. In particular, it may be desired to verify that other wall segment motion has not been degraded due to optimization of septal wall motion. It may also be desirable to optimize one or more pacing intervals based on septal wall motion and other pacing intervals based on RV apical wall motion or the motion of other wall segments.

Figure 8:
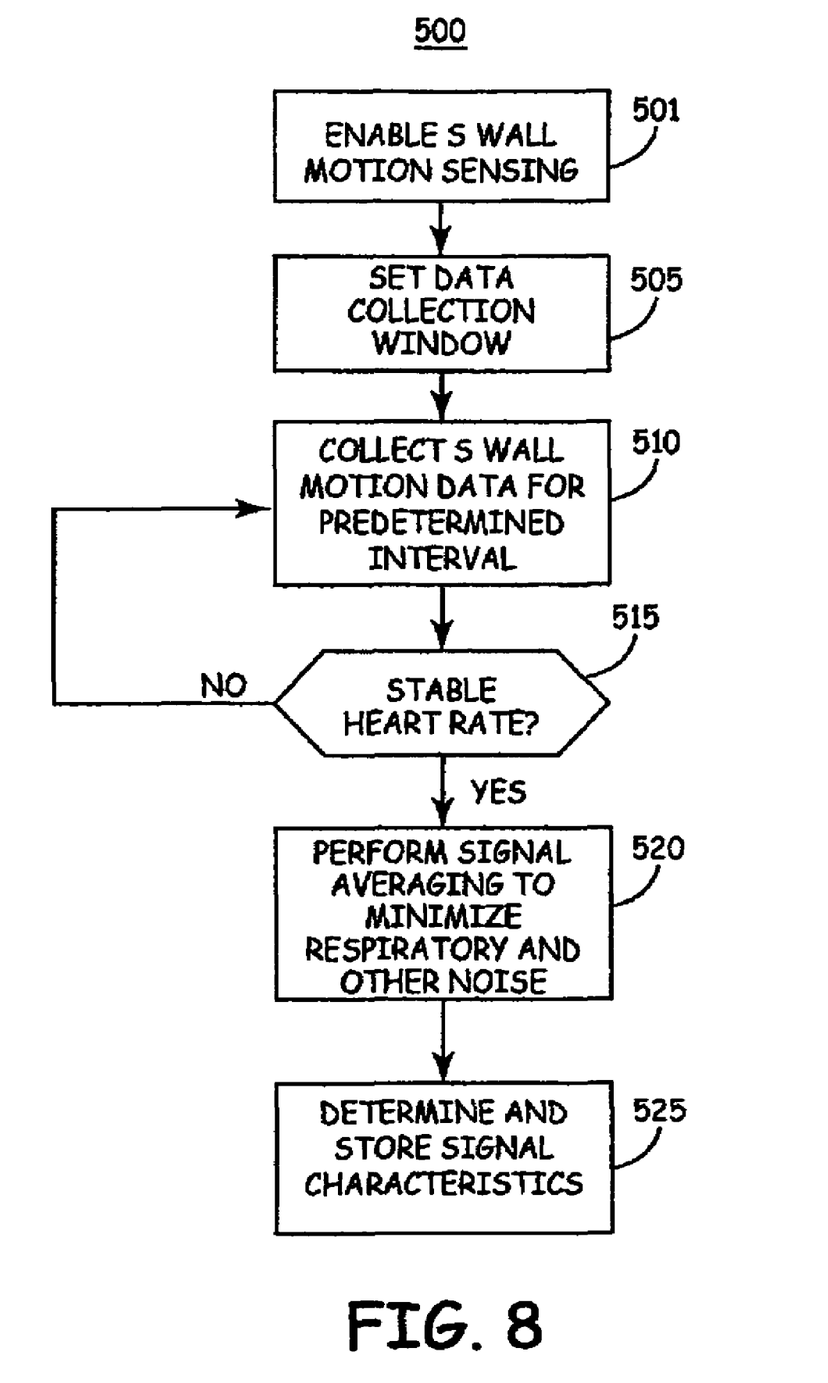
FIG. 8 is a flow chart summarizing steps included in a method for monitoring left ventricular function based on lateral wall motion.

FIG. 8 is a flow chart summarizing steps included in a method for monitoring left ventricular function based on lateral wall motion. As indicated previously, evaluation of left ventricular function is of interest for both diagnostic and therapeutic applications. Thus, it is recognized, that aspects of the present invention may be employed for monitoring purposes without optimization of a therapy delivery. As such, method 500 summarized in FIG. 8 may be implemented in an implantable or external device for monitoring cardiac function by deriving and storing a septal wall motion parameter from a sensed septal wall motion signal. The therapy delivery functions of such devices may be selectively disabled or, if enabled, the optimization of cardiac pacing intervals based on septal wall motion may be selectively enabled or disabled. Method 500 may alternatively be implemented in internal or external devices that do not include therapy delivery capabilities, but in association with an RA or RV lead equipped with a wall motion sensor, are capable of processing and storing septal wall motion data.

Septal wall motion may be sensed during a selected phase of the cardiac cycle on a continuous, periodic or triggered basis with the wall motion signal characteristic determined and stored after each predetermined interval of time or number of cardiac or respiratory cycles. For example, cardiac function may be evaluated on a periodic basis such as hourly, daily, weekly, or otherwise. Additionally or alternatively, cardiac function may be evaluated on a triggered basis, which may be a manual or automatic trigger. Automatic triggers may be designed to occur upon the detection of predetermined conditions during which cardiac function evaluation is desired, such as a particular heart rate range, activity, or other conditions.

In one embodiment, septal wall motion is monitored continuously and storage of septal wall motion data is triggered upon the detection of predetermined data storage conditions, such as, but not limited to, a heart rate, activity, or a condition relating to septal wall motion. For example, septal wall motion may be sensed continuously, and, if a septal wall motion parameter crosses a threshold or satisfies other predetermined data storage criteria, septal wall motion parameter(s) are stored.

Manual triggers for septal wall motion sensing and/or data storage may be delivered by a clinician or by a patient, for example when the patient feels symptomatic. Methods for manually triggering the storage of physiological data in an implantable device are generally described in U.S. Pat. No. 5,987,352 issued to Klein, et al., hereby incorporated herein by reference in its entirety.

Method 500 begins at step 501 when septal wall motion sensing is enabled according to the mode of operation of the monitoring device, which as just described, may be continuous, periodic, automatically- and/or manually-triggered monitoring. At step 505, a septal wall motion data collection window is set as described previously. At step 510, septal wall motion data is acquired for a predetermined interval of time or number of cardiac or respiratory cycles. At step 515, heart rate stability is verified as described previously. The wall motion signal is averaged over the number of cardiac cycles collected at step 520 to minimize respiratory or other noise. At step 525, a characteristic of the averaged signal is determined and stored as an indication of cardiac function. Other physiologic or parametric data may be stored with the cardiac function data such as heart rate, date and time of day, pacing modality and parameters, and/or any other physiological data that may be sensed by the monitoring device such as patient activity, blood pressure, etc.

The motion signals may be processed in a variety of ways as known in the art. For example, a signal may be filtered, rectified, mathematically integrated (or derived), and the like. With regard to filtering a septal acceleration signal, an about 5 to about 100 Hz band-pass filter provides a relatively clean signal from which the peaks are readily picked-off. A first integral of an accelerometer signal yields a velocity signal and a second integral yields a signal of displacement of the sensor. Thus, according to the present invention, each one or a discrete pair of acceleration, velocity and/or displacement measurements may be used to determine the optimal pacing interval. For example, a relatively high acceleration signal of very short duration likely indicates less overall septal "motion" than a slightly lower magnitude acceleration signal of relatively long duration.

Accordingly, one embodiment of the present invention utilizes a displacement metric of septal wall tissue as mathematically integrated from an accelerometer adapted to couple to septal wall tissue. According to this embodiment, a pacing interval of interest is slewed through a range of values and all discrete values of the second mathematical integral of the resulting acceleration signal are compared to identify the minimum displacement produced by a given one of said range of values. This minimum displacement value is then programmed for use during delivery of cardiac pacing therapy.

A cross-checking process to validate the selected minimum value comprises a comparison of the acceleration signal from which displacement was obtained. In the event that selected one of the underlying acceleration signals was of high magnitude and short duration while another was close in magnitude to the selected one—but of much longer duration—a cross-check processing technique could be set to declare a preferred value. Such a technique could be programmable so that a priority ranking is used for a primary, secondary and tertiary signal. In one form of this embodiment of the present invention, displacement could be the primary, most heavily weighted signal, acceleration could be the second-weight signal, and velocity would then be the third-weight signal. The present invention is intended to cover each alternative form of the three signals.

An aspect of the present invention closely related to the cross-checking process just described relates to validating the selected pacing interval(s) with an additional transducer. For example, a pressure or flow sensor or other mechanically-based transducer coupled to sense cardiac activity can be used to validate the optimized pacing intervals according to the present invention (based on one or more of acceleration, velocity, and displacement).

When the methods of the present invention are implemented in an implantable device, stored data available through uplink telemetry to an external device can be displayed and/or reviewed by a physician. When such methods are implemented in an external device, a display of cardiac function data may be updated each time a septal wall motion signal characteristic is determined.

Thus, a method and apparatus have been described for monitoring septal wall motion and optimizing a cardiac therapy based on minimal septal wall acceleration measured using a medical electrical lead equipped with an acceleration sensor. The methods described herein may advantageously be applied in numerous cardiac monitoring or therapy modalities including chronic or acute applications associated with implantable or external devices.

As is known in the art, besides the transducers described hereinabove, other types of transducers may be used provided, in general, that such transducers are hermetically sealed, are fabricated (on least on the exterior surfaces) of substantially biocompatible materials and appropriately dimensioned for a given application. With respect to appropriate dimension, a transducer intended for transvenous deployment should be capable of catheter or over-the-wire delivery. Thus, the radial dimension should be on the order of less than about 11 French and preferably about less than eight French. Also, the transducer should be somewhat supple, and not too long, in the longitudinal dimension so that the transducer can safely navigate the venous system, pass through the coronary sinus and enter vessels branching from the coronary sinus (e.g., the great cardiac vein, and the like). These dimensions can be relaxed for a transducer intended for deployment though a portion of the chest (e.g., a thoracotomy) with an affixation mechanism adapted to mechanically couple to wall tissue.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electric signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describe the internal mechanism of the accelerometer, include spring-retained seismic mass. In most accelerometers, acceleration forces a damped seismic mass that is restrained by a spring, so that it moves relative to the casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot, only the seismic mass primary transducer will be discussed.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20–60 Hz, depending on the stiffness of the spring, and have a high-level output signal. They also have a lower frequency response than most other accelerometers, usually between 15–30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

Thus, those of skill in the art will recognize that while the present invention has been described herein in the context of specific embodiments, it is recognized that numerous variations of these embodiments may be employed without departing from the scope of the present invention. The descriptions provided herein are thus intended to be exemplary, not limiting, with regard to the following claims.

For example, the methods according to the present invention may be performed automatically by a programmable IPG or ICD or may be performed acutely in a clinical setting. The methods are inherently susceptible of implementation by a microprocessor-controlled apparatus and, as such, may comprise executable instructions stored upon a computer readable medium and the like. In addition to the use of the motion sensors 11,60 disclosed herein, said motion sensors 11,60 may be used for arrthymia detection, capture detection for any paced chamber of the heart, and/or providing a rate responsive capability to an IPG or ICD by deriving an activity signal for a patient.

In one form of the present invention long-term trend information regarding septal wall motion may be derived during periods of time when CRT or other heart failure pacing therapy is not provided (e.g., during delivery of an atrial-based pacing therapy regime such as AAI, ADI, AAI/R, ADI/R and the like—with back-up mode switching in the event of loss of AV conduction, etc.). As a result, the potentially curative effects of such therapy can be gauged. One example of this form of the present invention utilizes a mechanically derived aspect of septal wall motion to determine whether reverse modeling of a previously failing heart (e.g., a heart suffering from effects of dilated cardiomyopathy) has reached a level wherein CRT may cease or be applied only periodically. One advantage of this form of the present invention relates simply to reduction in duty cycle of a CRT pacing engine (e.g., from a triple chamber pacing regime to a single or double chamber pacing regime). According to this form of the present invention, from time-to-time when CRT or other bi-ventricular pacing is not being delivered septal motion data is collected and stored. Thereafter, the past-trend of septal motion can be compared to current septal wall motion activity to derive an indication whether or not the positive effects of reverse remodeling are occurring. In a very simple form of this embodiment of the invention, periodically the bi-ventricular pacing therapy is switched to an atrial-based pacing therapy and the septal natural, or intrinsic, wall motion measured. If said wall motion exceeds a preset threshold, then the bi-ventricular therapy is again applied. If not, then the bi-ventricular therapy may be terminated until such time as uncoordinated ventricular motion is again detected.

In the case of arrthymia detection, atrial flutter/fibrillation (AF) and ventricular fibrillation (VF) are readily distinguishable via manual or machine inspection of the output from a motion sensor 11,60. Similarly, in the case of capture detection the output from a motion sensor 11,60 according to the present invention provides a reliable means of ascertaining whether delivery of pacing therapy provides an evoked response. That is, within a very short period of time following delivery of pacing therapy to a chamber of a heart (e.g., within about five to 50 ms) the output signal from a motion sensor 11,60 will either provide a corresponding deflection as the evoked depolarization wavefront passes the sensor 11,60 or when an actual physical contraction of cardiac myocytes occurs. In this regard, same- and cross-chamber capture detection readily and accurately reflects whether an adequate amount of energy from the pacing therapy is being delivered to a chamber of the heart. Thus the present invention enables pacing (energy) threshold testing and, perhaps more directly, the respective temporal disposition between delivery of pacing therapy and the refractory/non-refractory portions of a cardiac cycle for both the atria and ventricles. Since a motion sensor 11,60 useable in conjunction with the present invention can continuously provide a motion signal even if co-located with a pacing (or cardioversion/defibrillation) electrode this aspect of the present invention provides benefit over other modalities for optimizing CRT, or halting delivery of CRT (or other bi-ventricular pacing therapy) in the event that septal wall motion decreases below a threshold, for maximum pumping efficiency with minimal deleterious septal wall motion in a variety of pacing modes.

The invention claimed is:

1. A system for providing optimized cardiac chamber synchronization to a patient during delivery of cardiac pacing therapy, comprising:
   means for sensing a depolarization event of and/or providing a pacing stimulus to at least two chambers of a heart;
   a single means for sensing acceleration, velocity or displacement of only a portion of an interchamber septal wall tissue of the heart disposed between said at least two chambers of the heart and providing a displacement signal thereof to the means for sensing a depolarization event and/or providing pacing stimulus; and means for adjusting the timing for providing pacing stimulus to said heart to reduce or maintain the magnitude of the sensed displacement signal.

2. A system according to claim 1, wherein the at least two chambers of the heart comprise a left ventricle and a right ventricle.

3. A system according to claim 1, wherein the means for sensing comprises an accelerometer.

4. A system according to claim 3, wherein the accelerometer comprises a multi-axis accelerometer.

5. A system according to claim 1, wherein the means for adjusting timing is a programmable implantable medical device, said programmable implantable medical device further comprising a therapy delivery means for providing electrical stimulation therapy to said chambers and at least a one of: an adjustable V—V delay interval, an adjustable A—A delay interval, an adjustable A-V delay interval.

6. A system according to claim 3, further comprising an accelerometer adapted to be coupled to a portion of inter-atrial septal tissue.

7. A system according to claim 1, wherein said means for sensing acceleration, velocity or displacement comprises a one of: an optical sensor; an acoustical sensor; a Hall effect sensor; a sensor having piezoelectric-, inductive-, capacitive-, resistive-elements, said sensor producing a variable signal proportional to septal wall motion or acceleration.

8. A method for providing optimized, closed-loop interchamber depolarization synchronization to a patient, consisting of:
providing pacing stimulus to at least two chambers of a heart;
sensing acceleration, velocity, or displacement using only portion of interchamber septal wall tissue of the heart and providing a displacement signal thereof; and
adjusting a delay interval for a pacing stimulus to a one of said at least two chambers of the heart to reduce or maintain the magnitude of the displacement signal.

9. A method according to claim 8, wherein said at least two chambers comprise a left ventricle and a right ventricle.

10. A method according to claim 8, wherein said means for sensing comprises an accelerometer.

11. A method according to claim 10, wherein said accelerometer comprises a multi-axis accelerometer.

12. A method according to claim 10, wherein the means for adjusting timing is a programmable implantable medical device, said programmable implantable medical device further comprising a therapy delivery means for providing electrical stimulation therapy to said chambers and further comprising, at least partially in response to the displacement signal, adjusting at least a one of:
an adjustable V—V delay interval,
an adjustable A—A delay interval,
an adjustable V-A delay interval,
an adjustable A-V delay interval.

13. A method according to claim 12, further comprising coupling an accelerometer to a portion of inter-atrial septal tissue.

14. A method according to claim 8, wherein said sensing step is carried out by a one of: an optical sensor; an acoustical sensor; a Hall effect sensor; a sensor having piezoelectric-, inductive-, capacitive-, resistive-elements, said sensor which produce a variable signal proportional to septal wall motion or acceleration.

15. A computer-readable medium for storing instructions to perform a method for providing optimized, closed-loop cardiac resynchronization therapy (CRT) to a patient, consisting of:

instructions for sensing a depolarization of and/or providing pacing stimulus to at least two chambers of a heart;
instructions for sensing acceleration, velocity or displacement using only a portion of interchamber septal wall tissue of the heart and providing a displacement signal thereof; and
instructions adjusting a delay timing interval for a pacing stimulus to a one of said at least two chambers of the heart to reduce or maintain the magnitude of the displacement signal.

16. A method for monitoring left ventricular function, comprising:
deploying a motion sensor to a fixed location relative to a portion of a septal wall wherein the sensor generates a motion signal proportional to motion of the septal wall;
opening a data collection window during a portion of a selected cardiac cycle phase;
storing the motion signal throughout at least a part of the portion of the data collection window for a predetermined time interval or for more than one cardiac cycle;
verifying a stability characteristic of the motion signal during the predetermined time interval or for more than one cardiac cycle; and
determining a signal characteristic from the stored signal that is representative only of septal wall motion during delivery of a one of: an atrial-based pacing therapy, an atrial-stimulation-only pacing therapy, a cardiac resynchronization therapy, a cardioversion therapy, a defibrillation therapy, a ventricular-stimulation-only pacing therapy.

17. A method according to claim 16, wherein said motion sensor is adapted to be disposed in a portion of inter-atrial tissue.

18. A method according to claim 17, wherein said motion sensor comprises an accelerometer.

19. A method according to claim 18, wherein the accelerometer comprises a uniaxial accelerometer having a longitudinal sensing axis substantially disposed orthogonal with respect to an adjacent surface of septal tissue.

20. A method according to claim 17, wherein said motion sensor comprises a biaxial accelerometer.

21. A method according to claim 17, wherein said motion sensor comprises a triaxial accelerometer.

22. A computer readable medium programmed with instructions for performing a method for optimizing cardiac pacing intervals in a device programmed to operate a bi-ventricular cardiac pacing modality, comprising:
instructions for sensing motion of a portion of a septal tissue of a heart with a deployed motion transducer and for providing a motion signal from the motion transducer;
instructions for opening a data collection window during a portion of a selected cardiac cycle phase;
instructions for storing the motion signal throughout at least a part of the portion of the data collection window for a predetermined time interval or for more than one cardiac cycle;
instructions for verifying a stability characteristic of the motion signal during the predetermined time interval or for more than one cardiac cycle;
instructions for averaging the stored motion signal; and
instructions for determining a signal characteristic from the averaged stored signal that is representative of only septal wall motion.

23. A computer readable medium according to claim 22, wherein said motion sensor is adapted to be disposed in a portion of inter-atrial septal tissue.

24. A computer readable medium according to claim 23, wherein said motion sensor comprises an accelerometer.

25. A computer readable medium according to claim 24, wherein the accelerometer comprises a uniaxial accelerometer having a longitudinal sensing axis disposed substantially perpendicular to an adjacent surface of tissue.

26. A computer readable medium according to claim 23, wherein said motion sensor comprises a biaxial accelerometer.

27. A computer readable medium according to claim 23, wherein said motion sensor comprises a triaxial accelerometer.

28. A computer readable medium according to claim 22, wherein the device comprises an implantable medical device.

29. A computer readable medium according to claim 25, wherein the first pacing electrode or the second pacing electrode further comprises a sense electrode in electrical communication with a sensing circuit coupled to the device and further comprising:
   instructions for measuring depolarization wave activity and at least temporarily storing at least one parameter related to the measured depolarization wave activity.

30. A method for optimizing cardiac pacing intervals based septal wall motion comprising;
   placing a motion sensor adapted for chronic in vivo implantation into electromechanical communication with only a portion of septal tissue so that the motion sensor generates a single
   dedicated motion signal proportional to the motion of the portion of septal tissue;
   enabling a temporal data collection window corresponding to a selected cardiac cycle phase;
   applying a cardiac pacing stimulus delivered according to a preselected set of test pacing parameters;
   sensing the motion signal during at least a part of the temporal data collection window or during a more than one cardiac cycle for at least some members of the preselected set of test pacing parameters;
   determining a signal characteristic from the sensed signal that is representative of relatively improved left ventricular function during each of the selected test pacing parameters; and
   storing a cardiac pacing timing parameter for a right ventricular pacing electrode and for a left ventricular pacing electrode that resulted in the single dedicated motion signal having the least magnitude.

31. An apparatus for optimizing cardiac function, comprising:
   means for sensing motion of a portion of ventricular septal tissue and providing a motion signal;
   means for stimulating a first ventricular chamber and a second ventricular chamber at the same moment and at different moments during a single cardiac cycle;
   means for storing the sensed motion signals during a temporal window when the first ventricular chamber and the right ventricular chamber are stimulated at the same moment and at different moments;
   means for mathematically integrating the sensed motion signals at least once during a period of time corresponding to when the first ventricular chamber and the right ventricular chamber are contracting;
   means for comparing the mathematically integrated motion signals and determining a set of pacing parameters corresponding to an integrated motion signal having the least magnitude; and
   means for storing the set of pacing parameters.

32. An apparatus according to claim 31, further comprising:
   means for applying the stored set of pacing parameters in a cardiac pacing device.

33. A method of determining if a bi-ventricular pacing therapy should be delivered to a patient, comprising:
   measuring a motion parameter of a portion of ventricular septal wall tissue during a period of time when an atrial-based pacing therapy is being delivered to a patient;
   comparing the measured motion parameter to either a predetermined therapy selection threshold or a prior measurement of ventricular wall motion of said patient which was obtained during a prior period of time when the atrial-based pacing therapy was being delivered; and
   in the event that the measured motion parameter either does not exceed the predetermined therapy selection threshold or exceeds the prior measurement, then withholding delivery of a bi-ventricular pacing therapy, or
   in the event that the measured motion parameter exceeds the predetermined therapy selection threshold or exceeds the prior measurement, then resuming delivery of the bi-ventricular pacing therapy.

34. A method according to claim 33, wherein said motion parameter comprises a one of: an acceleration parameter, a velocity parameter, a displacement parameter.

35. A method according to claim 33, wherein the bi-ventricular pacing therapy comprises a cardiac resynchronization therapy.

36. A method according to claim 33, wherein the atrial-based pacing therapy comprises a one of: an AAI pacing therapy, an ADI pacing therapy, an AAI/R pacing therapy, an ADI/R pacing therapy.

37. A computer readable medium for storing executable instructions for performing a method of determining if a bi-ventricular pacing therapy should be delivered to a patient, comprising:
   instructions for measuring a motion parameter of a portion of ventricular septal wall tissue during a period of time when an atrial-based pacing therapy is being delivered to a patient;
   instructions for comparing the measured motion parameter to either a predetermined therapy selection threshold or a prior measurement of ventricular wall motion of said patient which was obtained during a prior period of time when the atrial-based pacing therapy was being delivered; and
   instructions for withholding delivery of a bi-ventricular pacing therapy in the event that the measured motion parameter either does not exceed the predetermined therapy selection threshold or does not exceed the prior measurement, or
   instructions for resuming delivery of the bi-ventricular pacing therapy in the event that the measured motion parameter exceeds the predetermined therapy selection threshold or exceeds the prior measurement.

38. A method according to claim 37, wherein said motion parameter comprises a one of: an acceleration parameter, a velocity parameter, a displacement parameter.

39. A method according to claim 38, wherein the bi-ventricular pacing therapy comprises a cardiac resynchronization therapy.

40. A method according to claim 37, wherein the atrial-based pacing therapy comprises a one of: an AAI pacing therapy, an ADI pacing therapy, an AAI/R pacing therapy, an ADI/R pacing therapy.

* * * * *